(12) United States Patent
Jung et al.

(10) Patent No.: US 9,983,141 B2
(45) Date of Patent: May 29, 2018

(54) GAS SENSOR, REFRIGERATOR HAVING THE GAS SENSOR AND METHOD OF CONTROLLING THE REFRIGERATOR

(71) Applicant: Samsung Electronics Co., Ltd., Suwon-si (KR)

(72) Inventors: Hyun Joo Jung, Seoul (KR); Yong Won Jeong, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 14/666,654

(22) Filed: Mar. 24, 2015

(65) Prior Publication Data
US 2015/0377791 A1    Dec. 31, 2015

(30) Foreign Application Priority Data

Jun. 27, 2014    (KR) .................. 10-2014-0080162

(51) Int. Cl.
| | |
|---|---|
| *G01N 33/52* | (2006.01) |
| *G01N 31/22* | (2006.01) |
| *G01N 21/78* | (2006.01) |
| G01N 33/50 | (2006.01) |
| G01N 21/84 | (2006.01) |
| G01N 21/80 | (2006.01) |
| G01N 21/77 | (2006.01) |
| F25D 17/04 | (2006.01) |

(52) U.S. Cl.
CPC ......... *G01N 21/783* (2013.01); *G01N 31/221* (2013.01); *F25D 17/042* (2013.01); *F25D 2700/00* (2013.01); *G01N 21/80* (2013.01); *G01N 2021/773* (2013.01); *G01N 2021/7763* (2013.01)

(58) Field of Classification Search
CPC ...... G01N 33/525; G01N 33/52; G01N 33/50; G01N 33/48; G01N 21/8483; G01N 21/84; G01N 21/00; G01N 31/22; G01N 31/00
USPC ......................... 422/401, 403, 420
See application file for complete search history.

(56) References Cited

U.S. PATENT DOCUMENTS

2001/0045096 A1* 11/2001 Tatter .................... F25D 29/00
                                                             62/129
2005/0037485 A1*  2/2005 Rodgers ............... B01J 19/0046
                                                             506/43

(Continued)

FOREIGN PATENT DOCUMENTS

| EP | 2055347 | 5/2009 |
|---|---|---|
| JP | 2003-527594 | 9/2003 |

(Continued)

OTHER PUBLICATIONS

Peter Gacesa, "Alginates", *Carbohydrate Polymers* 0144-8617/88, 1988, pp. 161-182.

(Continued)

*Primary Examiner* — Christine T Mui
(74) *Attorney, Agent, or Firm* — Staas & Halsey LLP

(57) ABSTRACT

A gas sensor configured to be discolored in response to a pH change upon reaction with a target gas, a refrigerator including the gas sensor, and a method of controlling the refrigerator includes a hydrogel support discolored through reaction with the target gas, and the hydrogel support includes dye provided to be discolored in response to a pH change upon reaction with the target gas.

18 Claims, 20 Drawing Sheets

(56) References Cited

U.S. PATENT DOCUMENTS

| | | | | |
|---|---|---|---|---|
| 2006/0057022 A1* | 3/2006 | Williams | ............... | G01N 31/22 |
| | | | | 422/400 |
| 2006/0148958 A1* | 7/2006 | Haraguchi | ............. | C08K 3/346 |
| | | | | 524/445 |
| 2006/0228444 A1* | 10/2006 | Hahm | ..................... | F25D 23/12 |
| | | | | 426/7 |
| 2008/0199904 A1 | 8/2008 | Suslick et al. | | |
| 2011/0050431 A1* | 3/2011 | Hood | ................. | A47G 19/2227 |
| | | | | 340/603 |

FOREIGN PATENT DOCUMENTS

| | | | | |
|---|---|---|---|---|
| KR | 20-0335242 | 12/2003 | | |
| KR | 10-2012-0128964 | 11/2012 | | |
| KR | 10-2013-0042857 | 4/2013 | | |
| WO | 2004/025254 A2 | 3/2004 | | |
| WO | 2007/050463 A1 | 5/2007 | | |
| WO | WO2008/079024 A1 * | 7/2008 | ............. | G01N 21/80 |
| WO | WO 2012/091256 A1 * | 7/2012 | ............. | F25D 23/06 |
| WO | WO 2012/092181 A2 * | 7/2012 | ............... | C12Q 1/04 |

OTHER PUBLICATIONS

Extended European Search Report dated Nov. 19, 2015 in European Patent Application No. 15166060.2.

* cited by examiner

Color change principle of gas sensor using dye

FIG. 9

| Molec.<br>H-Const<br>pErinence<br>Feature | CO2 | O2 | Alcohol | Acetic acid | H2 | N2 | Aldehyde<br>(Acetaldehyde) | Sulfur compound<br>(Methylmercaptane) |
|---|---|---|---|---|---|---|---|---|
| H-Const | 0.03 | 0.001 | 100 | 5,000~10,000 | 0.0007 | 0.0006 | 10 | 0.3 |
| pErinence | Low | Non-existence | Low | High | Non-existence | Non-existence | Low | Low |
| Feature | Non-polarity | | Polarity | Polarity | Non-polarity | Non-polarity | Polarity | Non-polarity |

FIG. 10

| Molec. | Ammonia (NH3) | Sulfur compound (Methylmer captene) | Aldehyde (Acetaldehyde) | VOCs (pentane) |
|---|---|---|---|---|
| H-Const | 50 | 0.3 | 10 | 0.0008 |
| pH influence | High | Low | Low | Low |
| Feature | Polarity | Non-polarity | Non-polarity | Neutral polarity |

GAS SENSOR, REFRIGERATOR HAVING THE GAS SENSOR AND METHOD OF CONTROLLING THE REFRIGERATOR

CROSS-REFERENCE TO RELATED APPLICATIONS

This application claims the priority benefit of Korean Patent Application No. 10-2014-0080162, filed on Jun. 27, 2014 in the Korean Intellectual Property Office, the disclosure of which is incorporated herein by reference.

BACKGROUND

1. Field

The following description relates to a gas sensor configured to detect a concentration of a target gas, an electronic apparatus including the gas sensor, and a method of controlling the electronic apparatus.

2. Description of the Related Art

A gas sensor is an apparatus for measuring a concentration of a specific gas, and may be a semiconductor-type gas sensor, an electrochemical gas sensor, a catalytic combustion method gas sensor, an optical sensor, or the like, according to a measurement principle. Among these, the semiconductor-type gas sensor uses a method of measuring an effect of a change of a resistance element during oxidation or reduction of a measurement material, and the electrochemical gas sensor uses a method of measuring an amount of ions generated by oxidizing/reducing a gas dissolved in an electrolyte.

Because most gases, except for an insert gas, have a tendency of oxidation/reduction, in the semiconductor-type gas sensor or the electrochemical gas sensor, a cross-talk phenomenon occurs, in which another gas coexisting with a target gas to be measured is also measured. Accordingly, measurement sensitivity for selectively measuring a specific gas is limited.

In addition, the olfactory organ of a human body can detect a smelly gas to a ppb (parts per billion) level. However, because the current gas sensor has a lower measurement sensitivity or resolution than the olfactory organ of the human body, it is difficult to measure a gas of a ppm (parts per million) level or less.

SUMMARY

Therefore, in order to solve the problems, it is an aspect of the present disclosure to provide a gas sensor including dye provided in a hydrogel support to be discolored in response to a pH variation upon reaction with a target gas, a refrigerator including the gas sensor, and a method of controlling the refrigerator.

More specifically, it is an aspect of the present disclosure to provide a gas sensor including anthocyanin-based natural dye in a natural hydrogel support, a refrigerator including the gas sensor, and a method of controlling the refrigerator.

Additional aspects of the disclosure will be set forth in part in the description which follows and, in part, will be obvious from the description, or may be learned by practice of the disclosure.

In accordance with an aspect of the present disclosure, gas sensor may include a hydrogel support discolored through reaction with the target gas, wherein the hydrogel support includes dye provided to be discolored in response to a pH change upon reaction with the target gas.

In addition, the dye may include a natural dye or synthetic dye.

In addition, the natural dye may include an anthocyanin-based dye.

In addition, the natural dye may include vegetable dye extracted from at least one of red cabbage, blueberry, apple, pear, peach, asparagus, strawberry, pomegranate, and grape.

In addition, the synthetic dye may include at least one of chlorophenol red, methyl red, bromothymol blue, bromocresol green, nitrophenol, bromocresol purple, and alizarin.

In addition, the target gas may include volatile organic acid or base.

In addition, the volatile organic acid may include carbon dioxide or acetic acid, and the base may include ammonia.

In addition, the hydrogel support may be provided to solidify hydrogel.

In addition, the hydrogel support may have a crosslinked structure formed by a cross linking agent including a divalent cation.

In addition, the divalent cation may include calcium ion, and the cross linking agent may include calcium chloride.

In addition, the hydrogel of the hydrogel support may include natural hydrogel.

In addition, the hydrogel of the hydrogel support may include at least one of agar, agarose, sodium alginate, potassium alginate, rubidium alginate, calcium alginate, barium alginate, and propylene glycol alginate.

In addition, the hydrogel support may include at least one of glycerin, glycerol, propylene glycol, sorbitol, maltitol, polydextrose, triacetylglycerol, potassium lactate, isomalt, xylitol, sodium lactate, urea, glycosaminoglycan, poly vinyl alcohol, calcium chloride, and sodium chloride.

In addition, the gas sensor may be manufactured in a sheet type.

In addition, the gas sensor may further include a membrane coupled to one surface of the hydrogel support in contact with the target gas.

In addition, the gas sensor may be used to measure freshness, a degree of maturity, or a degree of fermentation of foods.

Next, according to an aspect, an electronic product may include a hydrogel support discolored through reaction with a target gas, wherein the hydrogel support includes a gas sensor including dye provided to be discolored in response to a pH change upon reaction with the target gas.

In addition, the electronic product may further include a storage container including a transparent section formed to be transparent at a portion or the entire thereof, wherein the gas sensor is disposed inside the transparent section of the storage container.

In addition, the gas sensor may have a membrane coupled to one surface of the hydrogel support in contact with the target gas.

In addition, the control unit may previously store information about a relation between a signal output from an optical sensor and the state of a target food, and determine the state of the target food according to the stored information.

Next, according to an aspect, a method of controlling an electronic product may include detecting a color of a gas sensor; determining a concentration of a target gas based on the detected color; and determining a state of a target food based on a concentration of the target gas.

In addition, the method may further include displaying the determined state of the target food.

In addition, the electronic product may be a refrigerator, and the method may further include controlling a temperature of the refrigerator based on the determined state of the target food.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 9 is a graph showing properties and Henry's constant according to a kind of a gas generated during fermentation of kimchi;

FIG. 10 is a graph showing properties and Henry's constant according to a kind of a gas generated during cold storage of meat;

DETAILED DESCRIPTION

Figure 1:
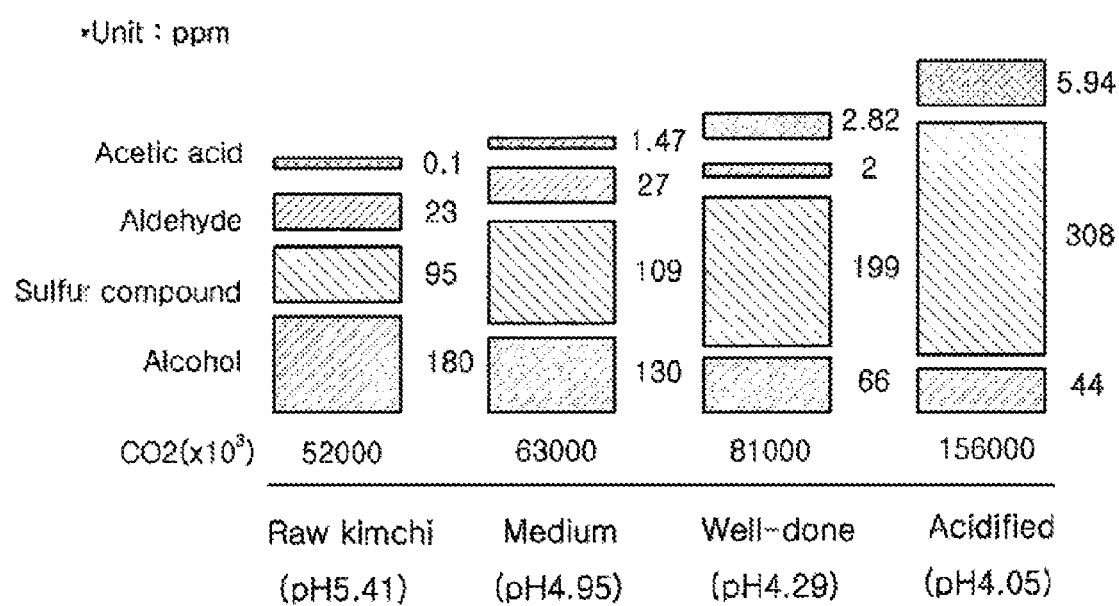
FIG. 1 is a graph showing a kind and a concentration of a gas generated according to a degree of maturity of kimchi.

Reference will now be made in detail to the embodiments of the present disclosure, examples of which are illustrated in the accompanying drawings, wherein like reference numerals refer to like elements throughout.

"Hydrogel" refers to a gel material using water as a dispersion medium and having a moisture-containing property in itself, and a phrase "a specific gas is dissolved in hydrogel" can be interpreted as "a specific gas is dissolved in a dispersion medium of hydrogel."

Because "the dispersion medium" refers to a medium constituting a colloidal dispersion system and "the hydrogel" uses water as "the dispersion medium", "the dispersion medium" of the hydrogel in which a specific gas is dissolved herein may be differentially expressed as "an aqueous solution."

Hereinafter, embodiments of the present disclosure will be described in detail with reference to the accompanying drawings.

A gas sensor according to an embodiment may be used in various fields in which a specific gas is measured. For example, a gas sensor may be used in a food management field, a medical diagnosis field, an environment management field, or a safety management field, for example. In order to specifically describe a configuration and an operation of the present disclosure, in the following embodiments, an example in which the gas sensor is used in the food management field for monitoring states of foods will be exemplarily described.

Figure 2:
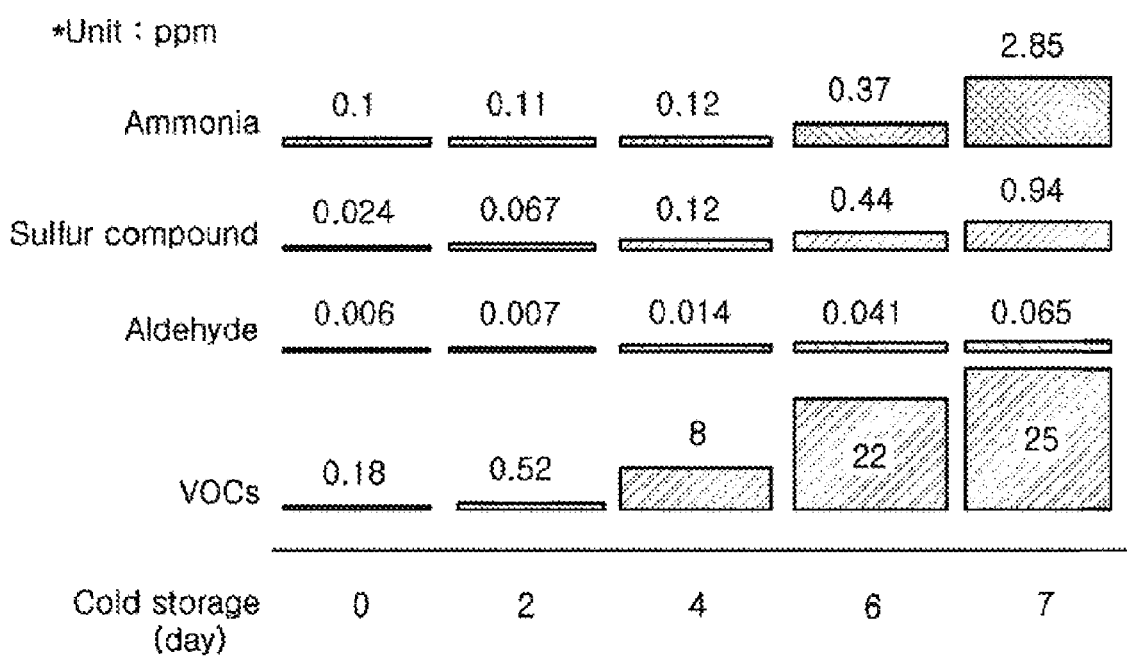
FIG. 2 is a graph showing a kind and a concentration of a gas generated according to a degree of maturity of meat.

FIG. 1 is a graph showing a kind and a concentration of a gas generated according to a degree of maturity of kimchi, and FIG. 2 is a graph showing a kind and a concentration of a gas generated according to a degree of maturity of meat.

Various kinds of gases are generated upon maturing or decay of foods, and a kind and an amount of the generated gas are largely affected by a degree of maturity of the foods and added spices, supplementary materials, or the like.

A gas ingredient of the generated gas closely related to the degree of maturity of the foods may be volatile organic acid, ammonia, or the like, and the gas ingredient is not detected in a fresh state but a concentration thereof is increased in comparison with the degree of maturity according to progress of the maturing.

Referring to FIG. 1, when kimchi, which is a fermented food, is matured, a gas such as acetic acid, aldehyde, sulfur compound, or alcohol is generated. Here, while a mainly generated gas is a gas such as aldehyde, sulfur compound, or alcohol, these gases are material-dependent gases generated from salted seafood, spices, and so on, and do not have direct linkage with respect to a level of fermentation or maturing of kimchi.

A gas directly related to the fermentation is a volatile organic acid gas generated as byproducts due to microorganisms, and acetic acid is exemplarily represented as the volatile organic acid gas in FIG. 1. While the acetic acid is represented as an example of the volatile organic acid gas of FIG. 1, the volatile organic acid gas is not limited thereto but should be understood as a concept including organic acid that can be easily volatilized in water including carbon dioxide.

As shown in FIG. 1, the acetic acid is hardly generated at the beginning of the fermentation but gradually increased as the fermentation progresses. However, the concentration is merely several ppms, which is remarkably lower than the other gases. Accordingly, in the case of the fermented food such as kimchi, the degree of maturity can be determined under the condition that the volatile organic acid having a concentration of 1 ppm or less is detected in the other gases having up to several hundred ppms.

In the case of the olfactory organ of the human, while varying among individuals, the volatile organic acid can be distinguished from the other gases even in the selectivity of several hundreds to one. However, most of the currently commercialized gas sensors cannot easily selectively measure only the volatile organic acid of about several ppms among the other gas ingredients of several hundred ppms.

Even in general foods other than the fermented food, the degree of maturity or the degree of decay can be recognized from the generated gas ingredient. In the case of the meat, amino acid is increased while protein is decomposed by microorganisms upon long term storage at a low temperature. The maturing of the meat may be a gradual decay process. As shown in FIG. 2, gases such as ammonia, sulfur compound, aldehyde, volatile organic compound (VOC), and so on, are generated in the amino acid metabolic process by bacteria propagating in the protein.

However, the gases of sulfur compound, aldehyde, and VOC are modified in the same gas according to the kind or portion of the meat. A single gas that can be an indicator of the degree of maturity or the degree of decay of the meat is ammonia. As shown in FIG. 2, because a generation amount of ammonia according to the degree of maturity of the meat is not large, the degree of maturity of the meat can be accurately determined under the condition that resolution of less than 1 ppm is provided.

As described above, in order to determine the degree of fermentation or the degree of maturity of the food, high selectivity and good resolution (resolution of sub ppm) should be provided such that a specific gas having a ppm level can be selectively detected in the other gas ingredient having several hundred ppms.

The gas sensor according to the embodiment may include dye in the hydrogel support to respond to a pH variation to be discolored such that high selectivity and good resolution can be implemented, and the gas sensor will be described below in detail.

Figure 3:
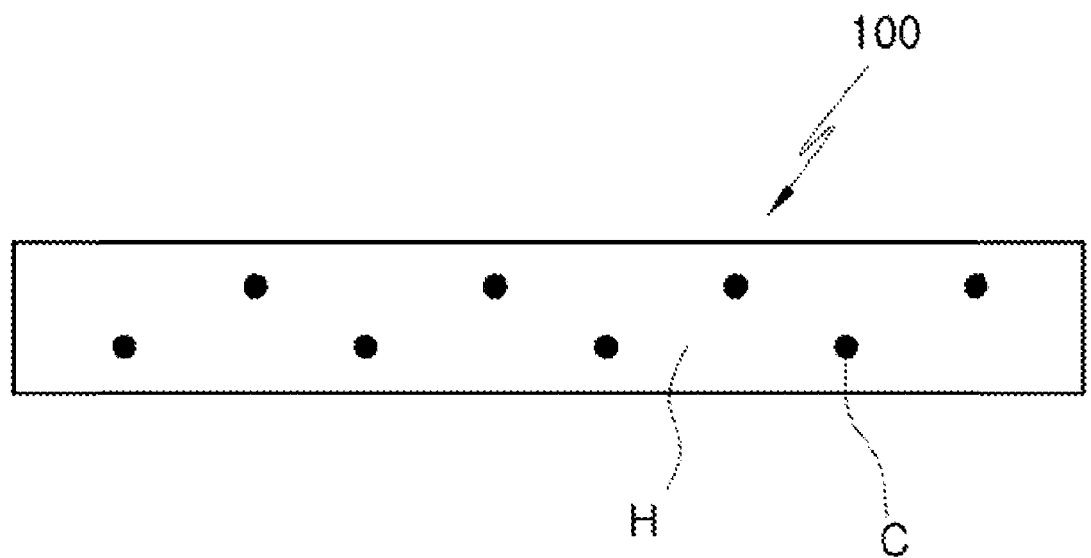
FIG. 3 is a view showing a gas sensor according to an embodiment.

FIG. 3 is a view showing a gas sensor 100 according to an embodiment.

Referring to FIG. 3, the gas sensor 100 according to the embodiment may be manufactured in a sheet shape. FIG. 3 shows an example of the gas sensor 100 manufactured in the sheet shape, but the shape of the gas sensor 100 is not limited thereto.

The gas sensor 100 may be implemented in various shapes according to a method of solidifying hydrogel, and descriptions of various processes such as a water film forming process, or the like, which is conventionally performed, may be omitted. Meanwhile, the gas sensor may be provided in a shape applied onto a specified container in a coating liquid state as described below, and for the convenience of description, the gas sensor 100 manufactured in the sheet shape will be exemplarily described below.

The gas sensor 100 according to the embodiment includes a hydrogel support H discolored through a reaction with a target gas, and the hydrogel support H includes dye C configured to be discolored in response to a pH variation upon reaction with the target gas. The dye C is discolored according to a concentration of a measurement target gas.

The hydrogel is a structure in which moisture is contained in a polymer net, which may be manufactured of a natural ingredient or manufactured through artificial synthesis. The gas sensor 100 according to the embodiment may use the hydrogel manufactured of the natural ingredient, and an ingredient may be added within a range that can be easily conceived of by those skilled in the art.

As described above, because the hydrogel can be manufactured of the natural ingredient, biocompatibility is high. The hydrogel has absorbency of absorbing water 200 to 300 times of the weight thereof, and a moisture-containing property of holding moisture in itself.

The hydrogel may be at least one natural ingredient such as agar, agarose, alginate, or propylene glycol alginate, for example. Hereinafter, for the convenience of description, the case in which the hydrogel includes alginate as a major ingredient will be exemplarily described.

Figure 4:
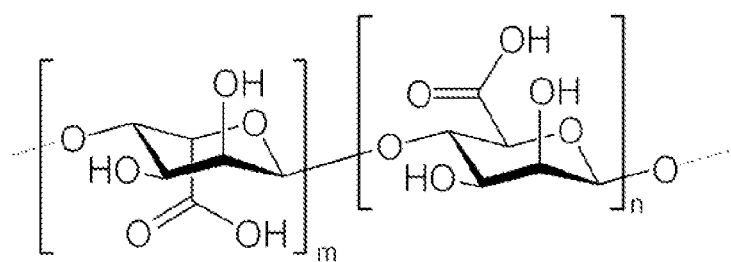
FIG. 4 is a view showing a structure of alginate as an example of a hydrogel ingredient.

FIG. 4 is a view showing a structure of the alginate as an example of the hydrogel ingredient. The alginate is an ingredient having viscosity that can be extracted from brown algae such as kelp, and has a hexagonal structure. More specifically, the alginate has a seat-type structure having a curved hexagonal surface.

The alginate has $C_6H_8O_6$ as a basic block unit, and has the entire structure similar to glucose. The alginate has a property exhibiting acidity due to a carboxyl group bonded to one end of the hexagonal structure. The hexagonal structure of the alginate is classified as an M type and a G type according to a direction of a carboxyl group (COOH) of a fifth carbon.

The alginate may be classified into sodium alginate, potassium alginate, rubidium alginate, and so on, as a hydrogen atom of the carboxyl group bonded to the fifth carbon is substituted with which univalent cation, or may be classified into calcium alginate, barium alginate, and so on, according to which cation electrostatically pulls a portion, from which the hydrogen ion is separated, to form a spherical shape.

The hydrogel may have a crosslinked structure formed by a cross linking agent including a divalent cation. The divalent cation may be a calcium ion, for example, and the cross linking agent may be calcium chloride, for example. Physical properties of the gas sensor 100 may be adjusted by adjusting a concentration of the cross linking agent or a speed of a gelation reaction of the hydrogel during solidification of the hydrogel.

Hereinafter, a process of forming the hydrogel support H by adding a calcium chloride solution serving as a hardener into the sodium alginate will be described.

Figure 5:
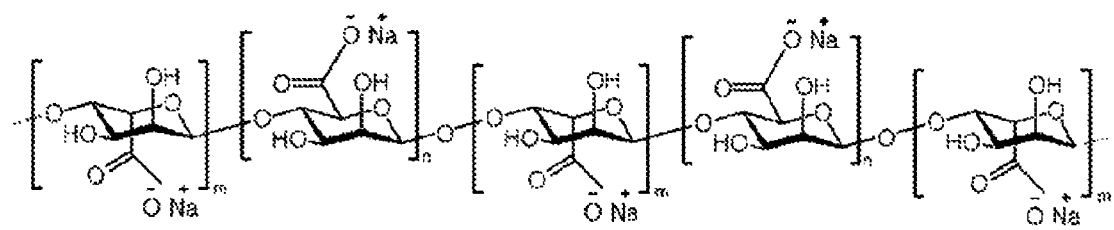
FIG. 5 is a view showing a structure of sodium alginate.
Figure 5:
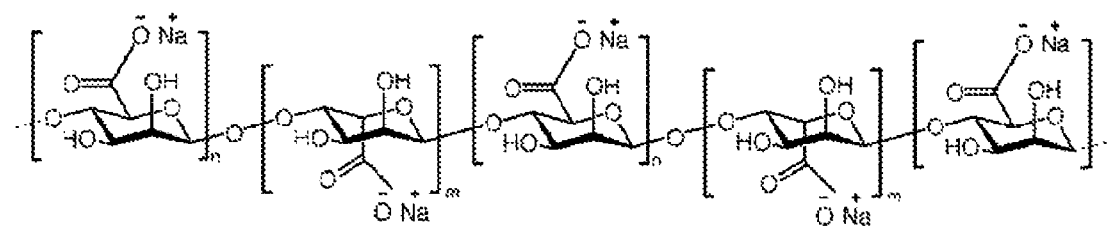
Figure 6:
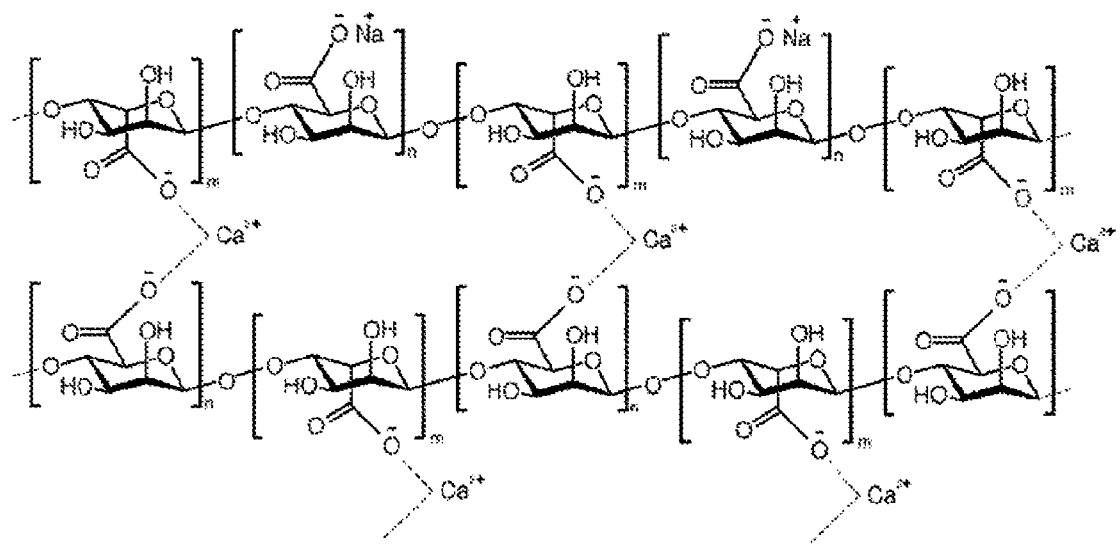
FIG. 6 is a view showing a gelation structure of alginate salt by calcium ions by addition of a sodium alginate solution of FIG. 5 into a calcium chloride aqueous solution.

FIG. 5 is a view showing a structure of the sodium alginate, and FIG. 6 is a view showing a structure of the alginate salt gelled by the calcium ion as the sodium alginate solution of FIG. 5 is added into a calcium chloride aqueous solution.

As shown in FIG. 5, when the alginate is added into the sodium chloride solution, the hydrogen atom of the carboxyl group bonded to the fifth carbon of the alginate is substituted with the sodium ion to form the sodium alginate. The sodium is a univalent cation that can be bonded to an anion without forming the crosslinked structure.

However, when the sodium alginate solution is added into the calcium chloride aqueous solution, the alginate salt is crosslinked by the calcium ion ionized in the calcium chloride aqueous solution to form the crosslinked structure as shown in FIG. 6.

The hydrogel support H may include at least one of glycerin, glycerol, propylene glycol, sorbitol, maltitol, polydextrose, triacetylglycerol, potassium lactate, isomalt, xylitol, sodium lactate, urea, glycosaminoglycan, poly vinyl alcohol, calcium chloride, and sodium chloride, for example to improve a moisture-containing property of the gas sensor 100. The hydrogel has a moisture-containing property in itself, and may selectively include the above-mentioned ingredient.

The hydrogel support H includes the dye C provided to be discolored in response to a pH variation upon reaction with the target gas.

The dye C may use a natural dye obtained form a natural material or a synthetic dye. In order to provide an advantage of the hydrogel that is harmless to a human body, the natural dye may be used.

The natural dye may include at least one of derivatives of anthocyanin-based dye, anthocyanidin-based dye, and anthocyanin or anthocyanidin-based dye (hereinafter, generally referred to as anthocyanin-based dye), for example.

The anthocyanin-based dye is one of vegetable dye extracted from at least one of red cabbage, blueberry, apple, pear, peach, asparagus, strawberry, pomegranate, and grape, and can be induced by various derivatives.

The synthetic dye may include at least one of chlorophenol red, methyl red, bromothymol blue, bromocresol green, nitrophenol, bromocresol purple, and alizarin, for example.

Hereinafter, a color change principle of the gas sensor 100 according to the embodiment using the dye C will be described.

As described above, because gas sensor 100 according to the embodiment employs a principle of the olfactory system of a human, a hydrogel support layer can perform a function of a slime layer of the epithelial tissue that collects odor molecules in air. That is, the hydrogel can selectively collect a water-soluble gas.

Previously, it has been described that the volatile organic acid gas and the ammonia gas can be used as important indicators to determine the degree of fermentation or the degree of maturity of the foods. Accordingly, the gas sensor 100 may use the volatile organic acid gas or the ammonia gas as the target gas. That is, the color of the dye C can be varied according to the concentration of the volatile organic acid or the ammonia gas.

The volatile organic acid gas and the ammonia gas are polarizable materials dissolved in water only, and can be dissolved in moisture contained in the hydrogel support H. Because the hydrogel has the moisture-containing property in itself, the hydrogel contains moisture therein as described above. For this reason, the hydrogel can selectively collect water-soluble molecules such as volatile organic acid or ammonia among various gas ingredients existing in an external environment of the gas sensor 100 except for fat-soluble molecules such as a sulfur compound or VOC. That is, the hydrogel functions to filter most of the sulfur compound and the VOC generated from the foods, and can improve selectivity with respect to the target gas of the gas sensor 100, which will be described below in related portions.

The volatile organic acid and the ammonia are commonly featured to cause a variation in concentration of the hydrogen ion as they are dissociated when dissolved in the aqueous solution. In the case of carboxylic acid (R—COOH), which is a typical volatile organic acid, the hydrogen ion is generated when dissolved in the aqueous solution to reduce a pH of the aqueous solution, and in the case of ammonia (NH3), the hydrogen ion of the aqueous solution is reduced when dissolved in the aqueous solution to increase the pH.

The gas sensor 100 according to the embodiment detects the pH variation according to a color change of the dye C included in the hydrogel. When the volatile organic acid or the ammonia is dissolved in the moisture absorbed in the hydrogel to cause the pH variation of the aqueous solution, presence and concentration of the target gas can be detected by observing the color of the dye C varied according to the pH variation.

Figure 7:
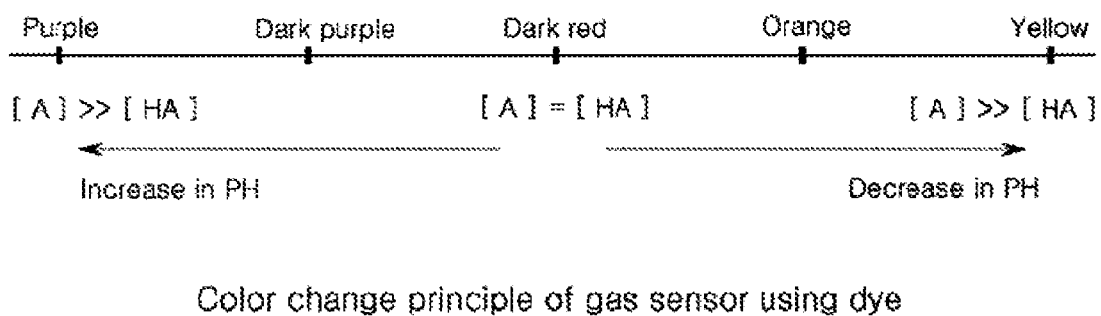
FIG. 7 is a view showing a principle of a gas sensor configured to detect a target gas by color change of dye.

FIG. 7 is a view showing a principle of the gas sensor 100 according to the embodiment to detect presence and concentration of the target gas by the color change of the dye C.

As described above, the pH of the dispersion medium is varied while absorbing or emitting the hydrogen ion when the volatile organic acid or the ammonia is dissolved in the hydrogel, an example of which is shown in FIG. 7. Here, the dye C dissolved in the dispersion medium is also polyprotic acid having various pKa and has different colors according to a hydrogen ion coupling pattern of the dye C.

When a shape of the dye C to which the hydrogen ion is coupled is represented as HA, the dye C is yellow, and when the shape of the dye C from which the hydrogen ion is separated is represented as A−, the dye C is purple. In this case, color of the dye C is varied according to a ratio of HA and A−. Here, the ratio of the HA and A− may be determined according to the pH of the solution. That is, the concentration of the dye C represented as HA is increased when the pH of the solution is low and the concentration of the hydrogen ion in the solution is high, and the concentration of the dye C represented as A− is increased when the pH of the solution is high and the concentration of the hydrogen ion ($H^+$) in the solution is low.

In brief, the volatile organic acid or the ammonia is dissolved in water to vary the pH of the solution and thus vary the ratio of the HA and A− of the dye C to cause a color change, the color change is determined according to the concentration of the target gas, and thus, presence and concentration of the target gas can be detected by observing or detecting the color change.

Hereinafter, the operation principle of the gas sensor 100 will be described while exemplifying the anthocyanin as the dye C using the acetic acid, which is a typical volatile organic acid, as a target gas.

First, a principle of securing reversibility of the gas sensor 100 according to the embodiment will be described.

When the acetic acid is dissolved in the hydrogel, the acetic acid is separated into acetate ion and hydrogen ion according to the following Chemical Formula 1, which is referred to as dissociation.

$$CH_3COOH \leftrightarrow CH_3COO^- + H^+ \quad \text{[Chemical Formula 1]}$$

A dissociation level of the acetic acid in the aqueous solution will be represented as an ionization constant or a dissociation constant according to the following Equation 1.

$$Ka = [CH_3COO^-][H^+]/[CH_3COOH] = 1.8 \times 10^{-5} \quad \text{[Equation 1]}$$

That is, the ionization constant (Ka) of the acetic acid is $1.8 \times 10^{-5}$, which may be represented as pKa 4.7 because the value is too small.

After the acetic acid is dissociated, original properties of the acetic acid no longer exist, and the dissociation is continuously performed to reduce the pH.

Figure 8:
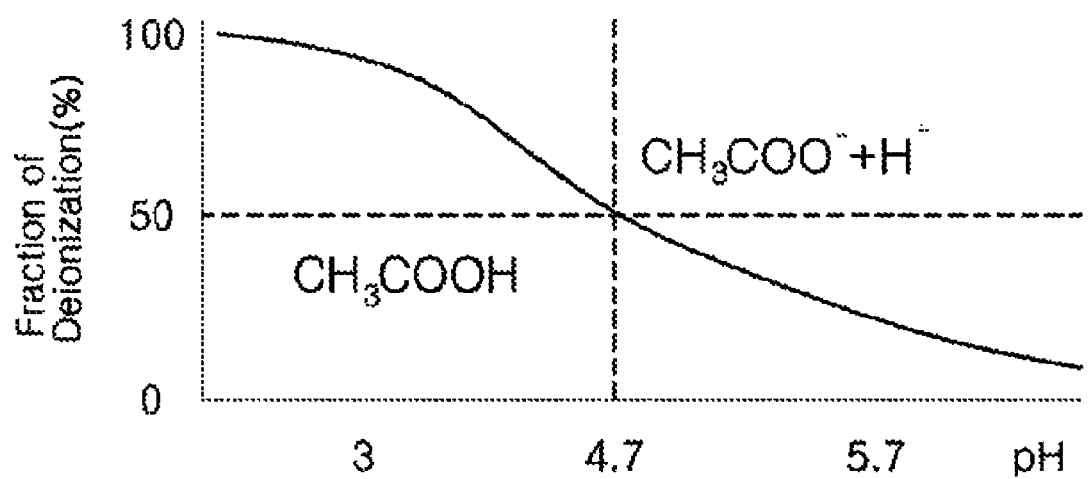
FIG. 8 is a graph showing a dissociation degree curve of acetic acid according to a pH change of an aqueous solution.

FIG. 8 is a graph showing a dissociation degree curve of the acetic acid according to the pH variation of the aqueous solution. Because a y-axis of the graph of FIG. 8 represents a fraction of deionization, the dissociation degree is decreased as the fraction is increased, and the dissociation degree is increased as the fraction is reduced.

Referring to FIG. 8, when the pH of the aqueous solution in which the acetic acid is dissolved is 4.7 equal to the pKa of the acetic acid, because the dissociation degree of the acetic acid is 50%, half of the acetic acid is dissociated to lose the properties thereof, and the remaining half is not dissociated maintains the properties.

When the pH of aqueous solution is smaller than 4.7, the dissociation degree of the acetic acid is abruptly decreased such that most of the acetic acid is not dissociated.

On the other hand, when the pH of the aqueous solution is larger than 4.7, the dissociation degree of the acetic acid is increased and the acetic acid is continuously dissociated. When the acetic acid is continuously dissociated in the aqueous solution, the hydrogen ion in the aqueous solution is increased to lower the pH. When the pH of the aqueous solution is lowered, the acetic acid having a certain concentration or more is not dissociated and remains as it is. The acetic acid, which is the volatile organic acid, has a property of being evaporated again when the acetic acid is present in the aqueous solution in a non-dissociated state.

Accordingly, when the aqueous solution is exposed to an environment in which the acetic acid gas having a certain concentration is present, the acetic acid dissolved in the aqueous solution is continuously dissociated to decrease the pH, and the acetic acid not dissociated in the aqueous solution is evaporated such that the gas introduced from the outside and the evaporated gas become a dynamic equilibrium state, i.e., an equilibrium state in which the pH of the aqueous solution is not varied.

In addition, when there is no acetic acid gas in the external environment, the acetic acid in the aqueous solution is continuously evaporated to increase the pH again. The gas sensor 100 can secure reversibility using such a principle.

Next, a principle in which the gas sensor 100 according to the embodiment selectively collects the target gas will be described in detail.

FIG. 9 is a graph showing properties and Henry's constant according to kinds of gases generated during fermentation of kimchi, and FIG. 10 is a graph showing properties and Henry's constant according to kinds of gases generated during cold storage of meat.

Molecules in a gaseous state have different water-soluble levels according to the kinds thereof. The Henry's constant may be an indicator that can exhibit a level at which a gaseous molecule is converted into a liquid state to be dissolved in water. As the Henry's constant is increased, a water-soluble property is increased, and as the Henry's constant is decreased, the water-soluble property is decreased.

Referring to FIG. 9, in the gases generated during maturing of kimchi, such as alcohol, aldehyde, and acetic acid have polarity, and carbon dioxide (CO2), oxygen (O2), hydrogen (H2), nitrogen (N2), and sulfur compound have non-polarity. The carbon dioxide (CO2), oxygen (O2), alcohol, hydrogen (H2), nitrogen (N2), and sulfur compound having non-polarity are not easily dissolved in an aqueous solution 110.

The gas having the largest Henry's constant is the acetic acid, which is the volatile organic acid. The Henry's constant is about 5000 to 10000, which is several hundred to several million times larger than the other gases. This means that the acetic acid can be dissolved several hundred to several million times more than the other gases.

Because the Henry's constant of the acetic acid is remarkably larger than alcohol or aldehyde as well as carbon dioxide (CO2), oxygen (O2), hydrogen (H2), nitrogen (N2), and sulfur compound, it will be appreciated that the gas sensor 100 including the hydrogel having water as the dispersion medium can collect the acetic acid from various kimchi fermentation gases at a very high sensitivity.

In addition, in the gases generated during maturing of kimchi, the acetic acid has the largest influence applied to the pH. Accordingly, the gas sensor 100 can measure the concentration of the acetic acid with good resolution. While alcohol, aldehyde, and sulfur compound can be extremely slightly dissolved in the aqueous solution, because an influence applied to the pH of the aqueous solution is very small, sensitivity of the gas sensor 100 can be secondarily improved.

Referring to FIG. 10, in the gases generated from the meat during cold storage, because the ammonia has the highest Henry's constant, the gas sensor 100 can collect the ammonia with high selectivity. In addition, because the ammonia has a large influence on the pH, the gas sensor 100 can measure the concentration of the ammonia with the best resolution.

Next, a color change principle of anthocyanin according to the concentration of the acetic acid will be described.

As described above, when the acetic acid is dissolved in the hydrogel, the pH of the hydrogel dispersion medium is varied. Here, the anthocyanin functions as an indicator, color of which is varied according to the pH. The anthocyanin exhibits a red color at acidity, a purple color at neutral, a blue color at basicity, and other colors according to the kind of the anthocyanin.

The anthocyanin may have a structure like Chemical Formula 2.

[Chemical Formula 2]

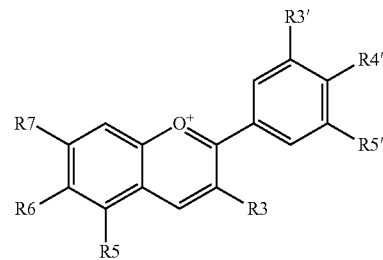

Referring to Chemical Formula 2, R3, R5, R6, R7, R3', R4', and R5' are substituents of the hydrogen atom of a benzene ring is substituted with a hydroxyl group, an alkyl group, or the like. That is, the anthocyanin is phenols in which a hydroxyl group (OH group) is bonded to the benzene ring, and has subacidity.

Here, when the anthocyanin is present in the basic solution, the anthocyanin is dissociated like phenol, the hydrogen ion is separated, and the oxygen atom exhibits an anion. The anion can form conjugation along with the pi bonding in the benzene ring. Because an energy difference between a ground state and an excited state is varied according to a variation in the conjugation structure and a kind of an absorbed wavelength is varied according to the varied energy difference, a kind of a complementary color entering the eye is varied to change the color.

The energy difference between the ground state and the excited state can be varied in the acidic or basic solution through the same principle. That is, equilibrium of the anthocyanin moves along the pH of the hydrogel dispersion medium varied according to the collected target gas, and various colors can be implemented because a major color is varied. The gas sensor 100 according to the embodiment can detect the target gas using the properties of the anthocyanin having the color varied according to the principle.

As described above, the structure and the operation principle of the gas sensor 100 according to the embodiment has been described. Next, a gas sensor 200 according to an embodiment will be described.

Figure 11:
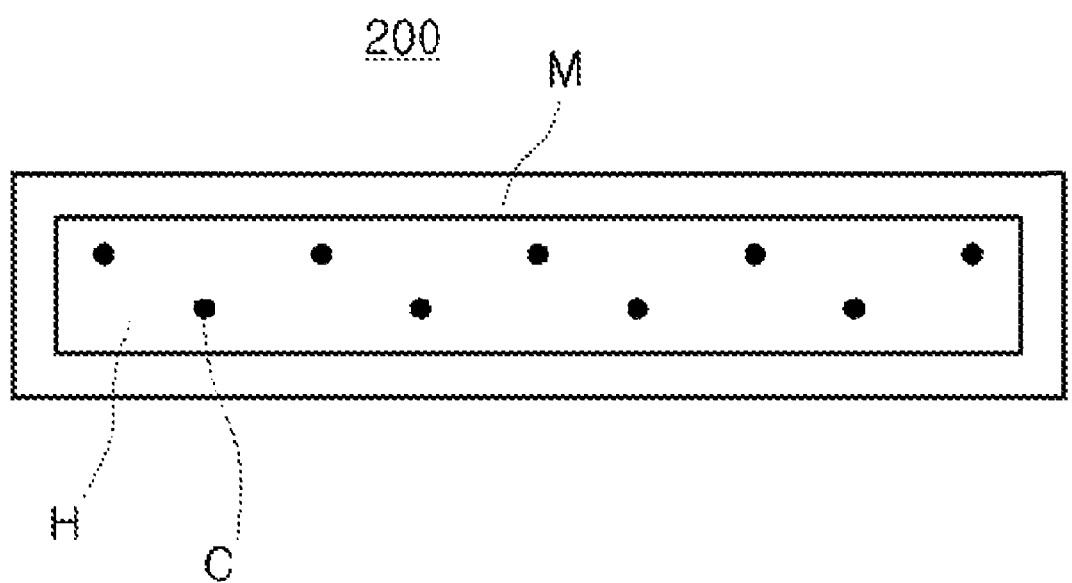
FIG. 11 is a view showing a structure of a gas sensor including a porous membrane according to an embodiment.

FIG. 11 is a view showing a structure of the gas sensor 200 including a porous membrane M.

Referring to FIG. 11, the gas sensor 200 also includes a hydrogel support H discolored in response to a target gas, and the hydrogel support H includes dye C discolored in response to a pH change upon reaction with the target gas. Hereinafter, overlapping description of the hydrogel support H and the dye C with respect to the gas sensor 100 will be omitted.

The gas sensor 200 according to the embodiment may have a structure in which the porous membrane M surrounds the hydrogel support H. The porous membrane M is formed of a material having gas permeability, and most of gas permeable resins including a porous polytetrafluoroethylene (PTFE) film may be used as the porous membrane.

The hydrogel is a material having a moisture-containing property in itself, forming the exterior of the gas sensor 200, and functions as a support configured to hold the dye C. However, because moisture may be excessively increased when humidity is high, the porous membrane M is advantageous in the prevention of excessive generation of moisture.

As described above, the gas sensor 200 including the porous membrane M has been described.

Hereinafter, an electronic product according to the embodiment will be described. The electronic product according to the embodiment is an electronic product to which a gas sensing technique is applied, and the same principle as the measurement of the concentration of the target gas can be applied using the gas sensors 100 and 200.

Figure 12:
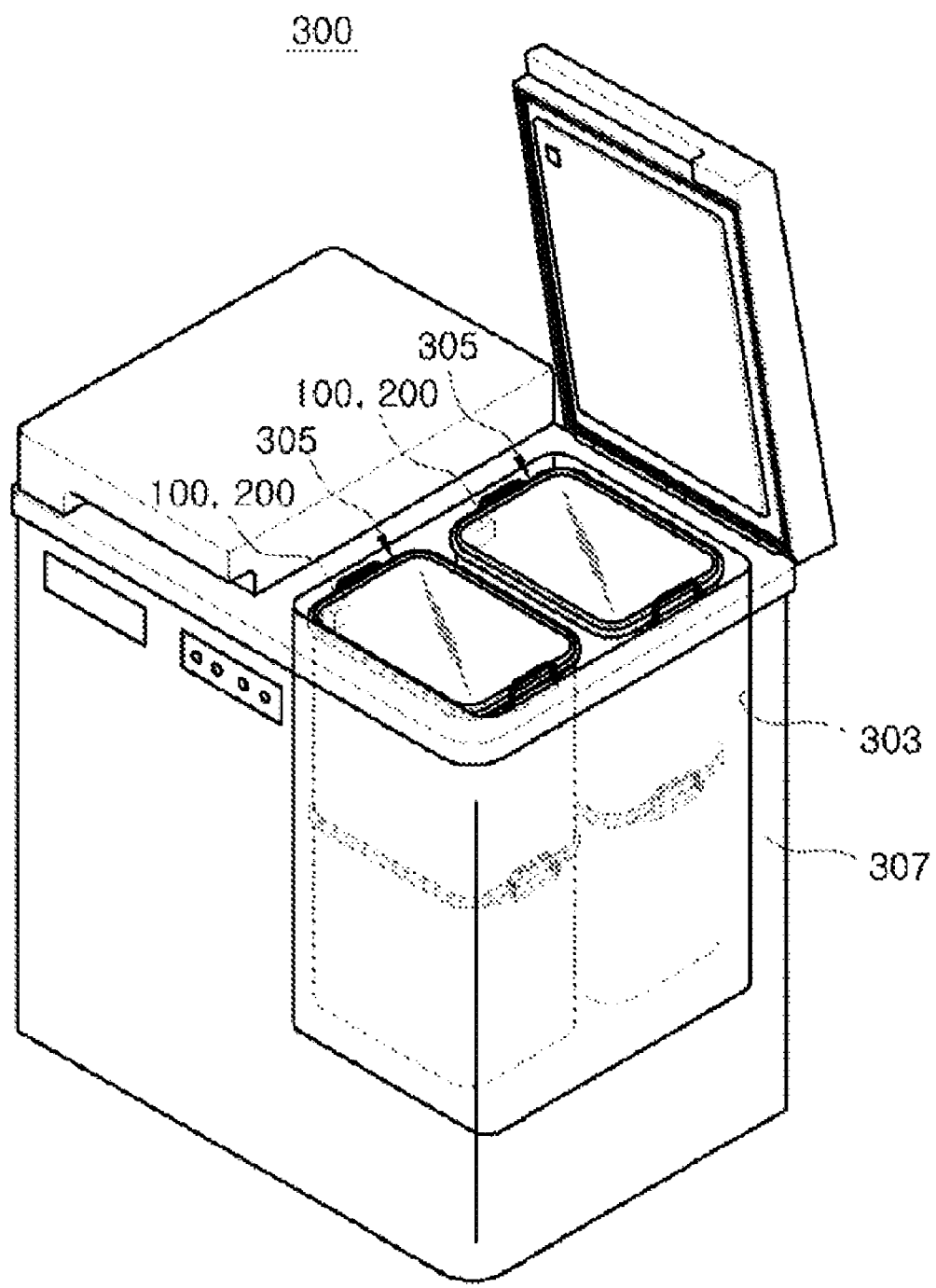
FIGS. 12 and 13 are perspective views of an electronic product according to the embodiment.
Figure 13:
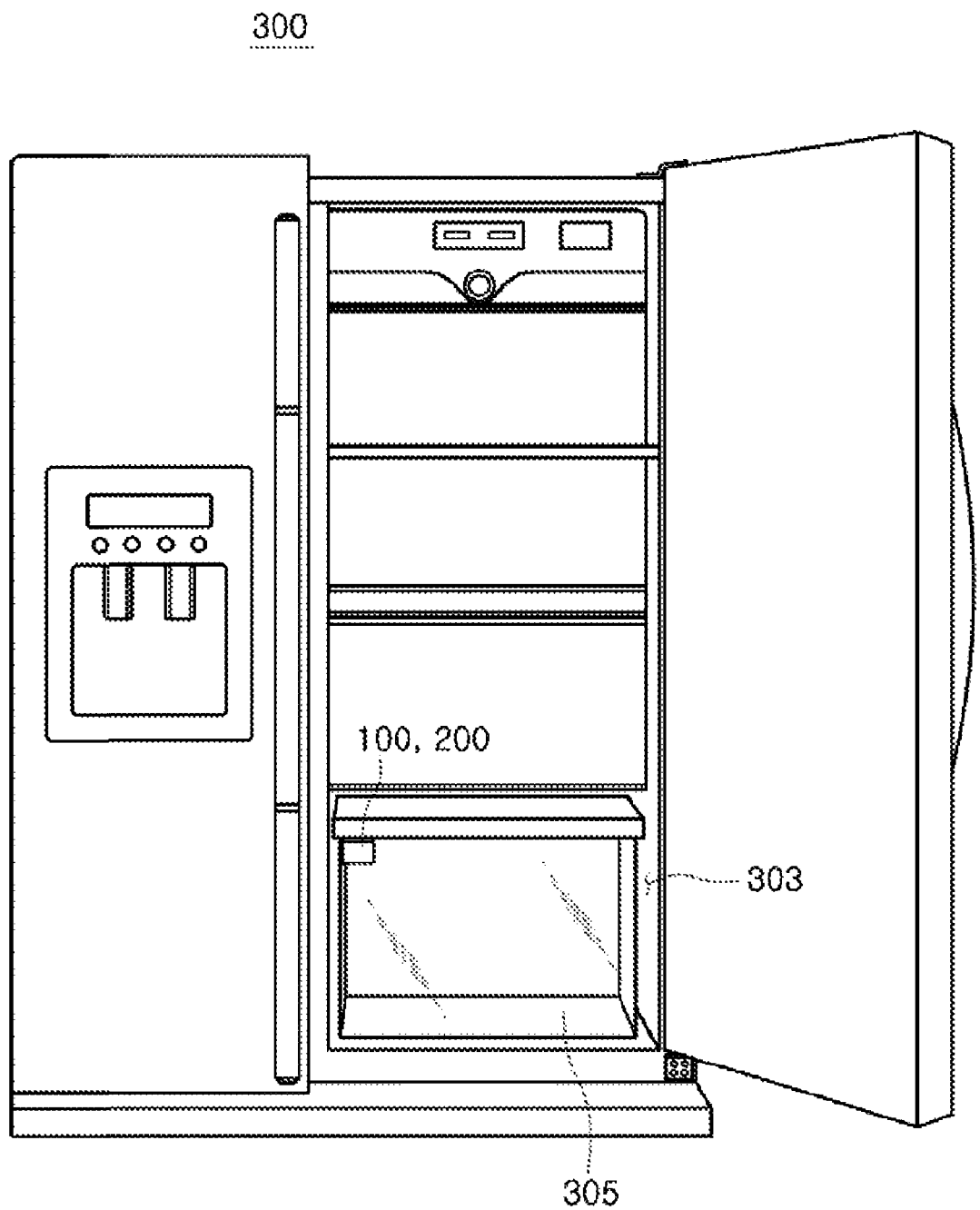

FIGS. 12 and 13 are perspective views of the electronic product according to the embodiment.

While various kinds of electronic products can be applied to the embodiment of the present disclosure, a refrigerator 300 configured to determine a state such as a degree of maturity or a degree of decay of foods based on measurement of the target gas will be exemplarily described.

The refrigerator 300 applied to the embodiment may be a kimchi refrigerator configured to store kimchi, or a general refrigerator, according to a use thereof. In addition, the refrigerator 300 may be classified as a stand type or a lid type according to a structure or shape thereof. Both of the stand type and the lid type may be the kimchi refrigerator or the general refrigerator. Because the refrigerator according to the embodiment is not limited to the kind or use, all type of refrigerators may be the refrigerator 300 according to the embodiment.

Hereinafter, the refrigerator 300 according to the embodiment will be described in detail with reference to FIGS. 12 and 13.

Referring to FIGS. 12 and 13, the refrigerator 300 is provided with a storage chamber 303 configured to store foods in a main body 307, and a storage container 305 disposed in the storage chamber 303 and separable from the refrigerator 300.

The gas sensors 100 and 200 are installed in the storage container 305 such that colors of the gas sensors can be varied according to a concentration of the target gas among the gases generated from the foods stored in the storage container 305. More specifically, the storage container 305 has a transparent portion formed at the entire surface or a portion thereof, or a transparent lid such that the gas sensors 100 and 200 are mounted therein.

As shown in FIG. 12, when the refrigerator 300 has a lid-type structure, the lid of the storage container 305 is transparent such that a user can directly check a state of foods as colors of the gas sensors 100 and 200 mounted therein are seen even when the storage container 305 is not taken out or the lid of the storage container 305 is not opened. As shown in FIG. 13, when the refrigerator 300 has a stand-type structure, a front surface of the storage container 305 is transparent such that the user can directly check a state of foods even when the storage container 305 is not taken out or the lid of the storage container 305 is not opened.

Figure 14:
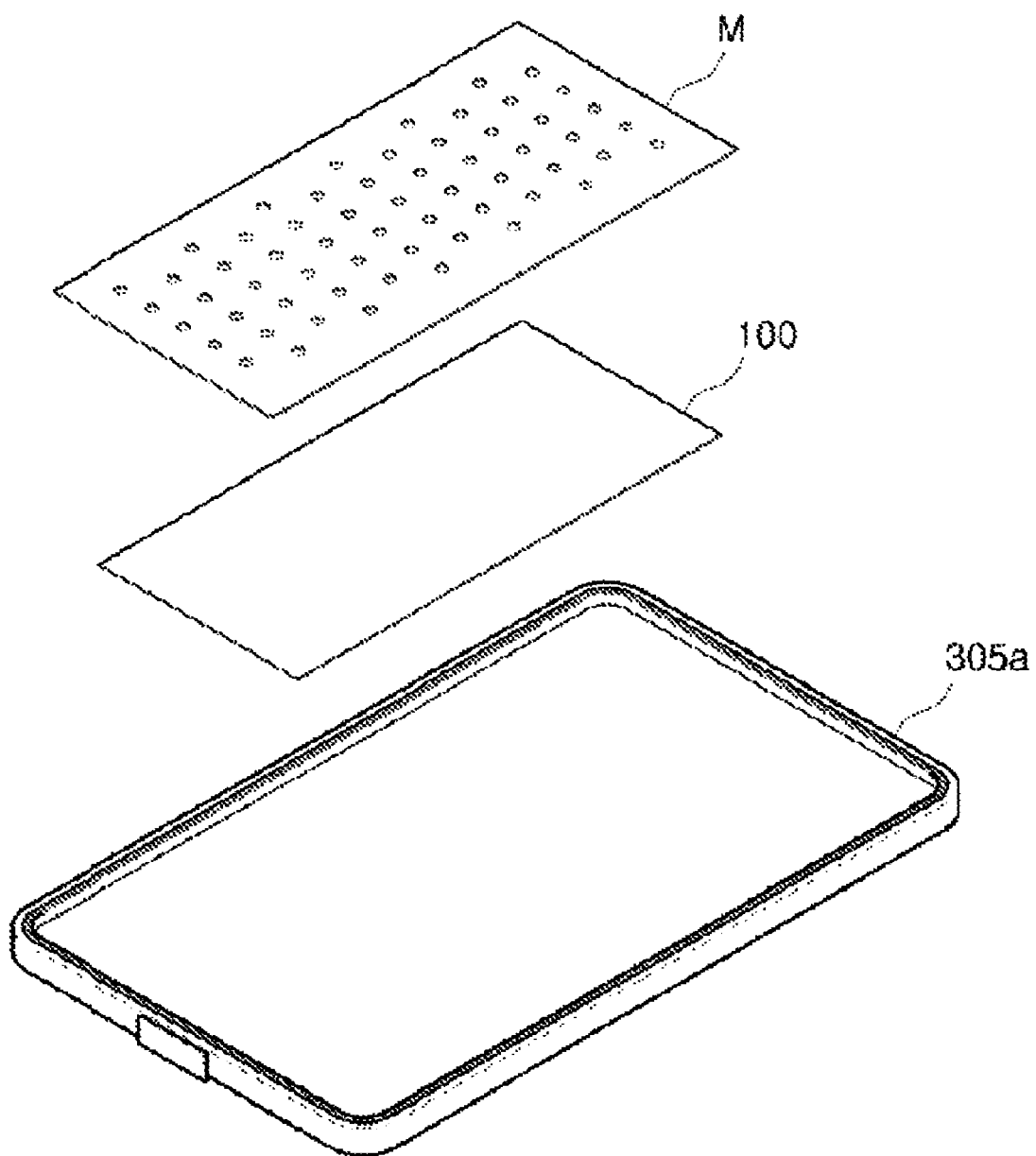
FIG. 14 is an exploded perspective view showing an example of a structure of a storage container when a lid of the storage container is transparent.

FIG. 14 is an exploded perspective view showing an example of a structure of the storage container 305 when a lid 305a of the storage container is transparent.

As shown in FIG. 14, the gas sensor 100 may be manufactured in a sheet shape to be mounted at an inner wall of the lid 305a of the storage container. In the case of the gas sensor 100 with no structure of the porous membrane M, in order to prevent generation of excessive moisture on the gas sensor 100, the porous membrane M may be mounted on one surface of the gas sensor 100 meeting with the target gas.

The porous membrane M may be provided to surround the hydrogel support H like the gas sensor 200.

The refrigerator 300 does not necessarily include the storage container 305, and the gas sensors 100 and 200 are not necessarily mounted in the storage container 305. The gas sensors 100 and 200 only need to be mounted in the refrigerator 300. However, when the gas sensors 100 and 200 are mounted in the closed storage container 305, because the sensors are not affected by the other gases except for the gases generated from the foods, the concentration of the target gas can be more accurately measured.

Meanwhile, the refrigerator 300 may employ both of a method of allowing a user to directly check color changes of the gas sensors 100 and 200 and a method of determining a state of foods by automatically detecting color changes of the gas sensors 100 and 200.

Figure 15:
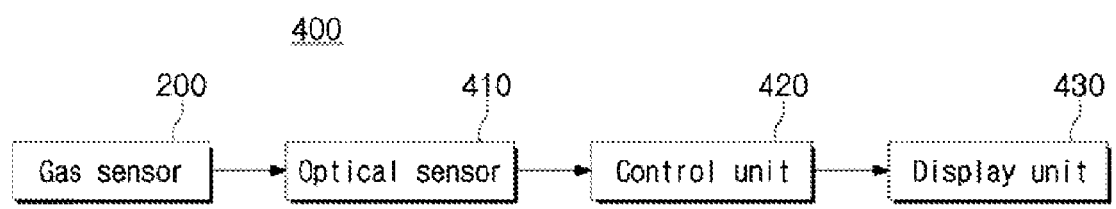
FIG. 15 is a control block diagram of an electronic product according to an embodiment, in which a color change is automatically detected.
Figure 16:
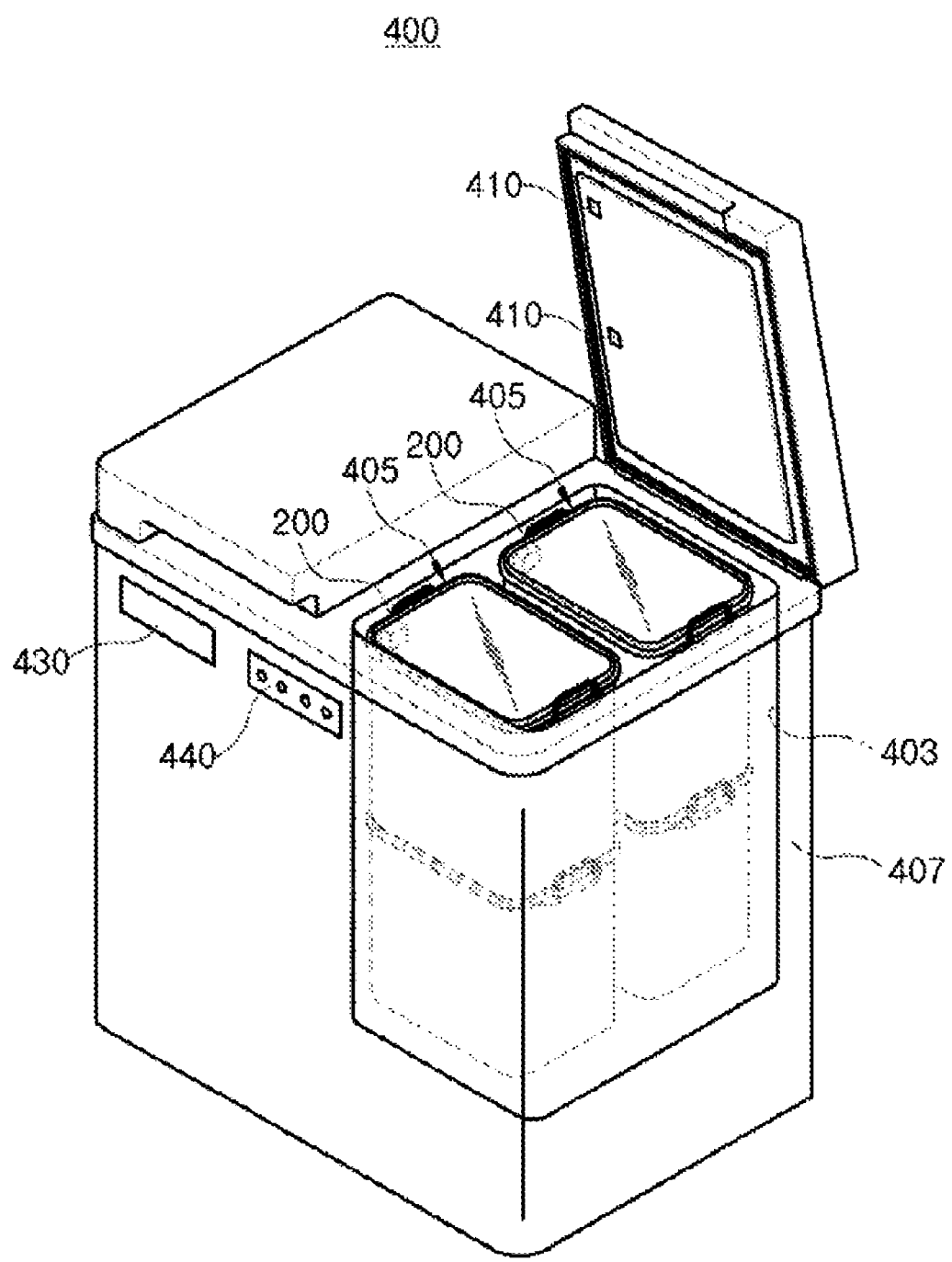
FIGS. 16 and 17 are perspective views of an electronic product according to an embodiment, in which a color change is automatically detected.
Figure 17:
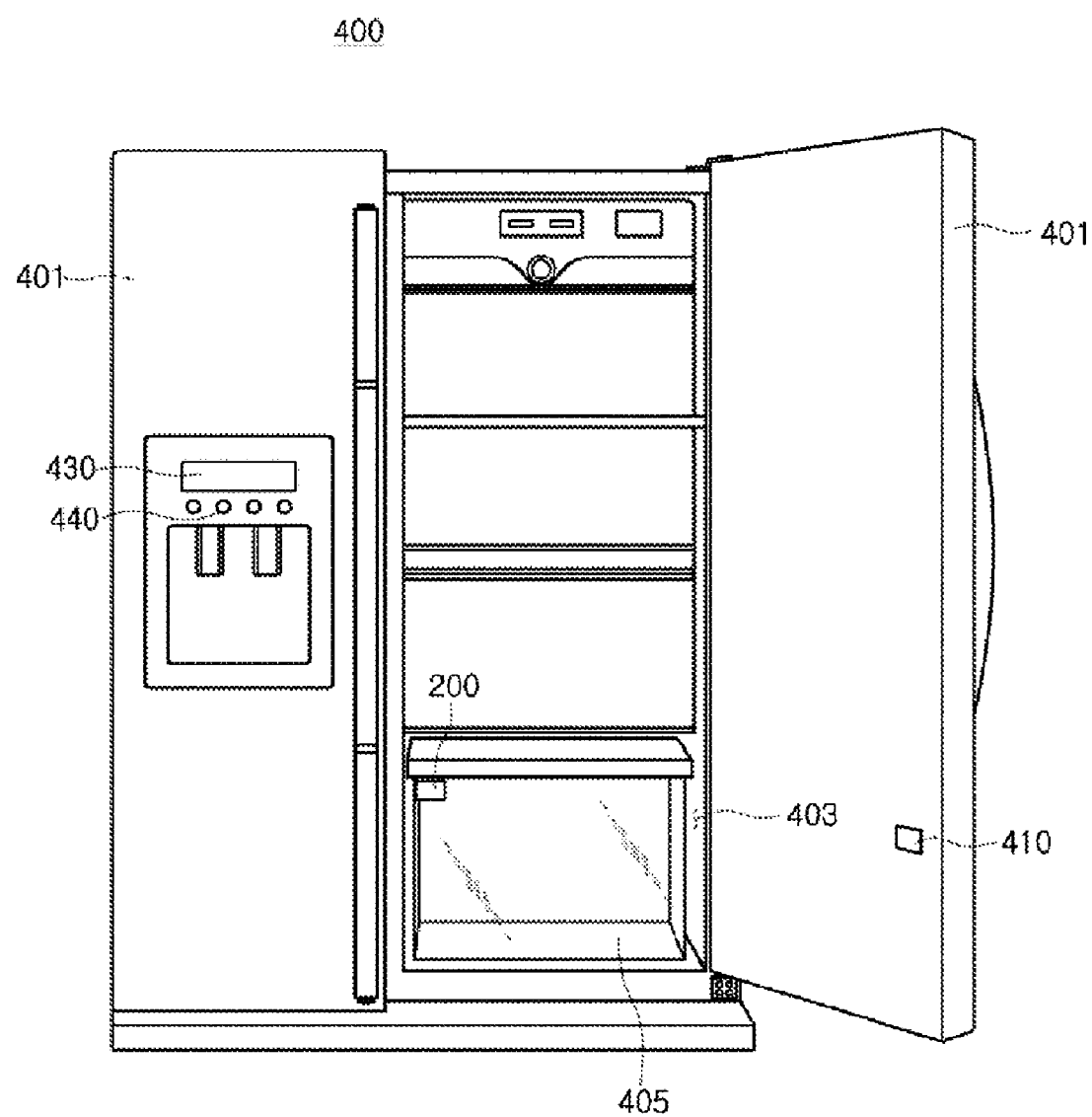

FIG. 15 is a control block diagram of an electronic product according to an embodiment configured to automatically detect a color change, and FIGS. 16 and 17 are perspective views of the electronic product configured to automatically detect a color change. An example of the electronic product of FIGS. 16 and 17 is exemplarily described as a refrigerator 400, and the case in which the gas sensor 200 including the porous membrane M is applied to the refrigerator 400 will be exemplarily described.

Referring to FIG. 15, the refrigerator 400 includes the gas sensor 200 according to the embodiment, an optical sensor 410 configured to detect a color of the gas sensor 200, a control unit 420 configured to determine a state of a target food based on a color of the gas sensor 200 detected by the optical sensor 410, and a display unit 430 configured to monitor a state of a determination target food.

Referring to FIGS. 16 and 17, the optical sensor 410 may be mounted on a portion directed toward the gas sensor 200 when a door 401 of the refrigerator 400 is closed. The optical sensor 410 and the gas sensor 200 are mounted at opposite positions in consideration of a relative positional relation, and the mounting position of the optical sensor 410 is not limited to the example shown in FIGS. 16 and 17.

When the gas sensor 200 is discolored according to the concentration of the target gas generated from the foods stored in the storage container, the color is seen from the outside through the transparent lid or the transparent body of the storage container 405, and when the door is closed, the optical sensor 410 can detect the color of the gas sensor 200 and an output signal can be transmitted to the control unit 420.

The control unit 420 can determine a state of the foods stored in the storage container 405 based on the output signal of the optical sensor 410. As described above, because a generated amount of the target gas is varied according to the degree of maturity or the degree of decay of the foods, the control unit 420 can store a database of the degree of maturity or the degree of decay of the foods according to the amount of the target gas, and determine the degree of maturity or the degree of decay of the foods corresponding to the output signal of the optical sensor 410.

Because the output value of the gas sensor 200 may be varied according to the kind and size of the foods, the state of the foods may be determined in consideration of information about the kinds and sizes of the foods input through an input unit 440 installed at the refrigerator 400.

According to the refrigerator 400 of the embodiment, the state of the foods can be recognized by opening the door and directly checking the color of the gas sensor 200, and the state of the foods determined by the refrigerator 400 itself using the optical sensor 410 may be checked through the information displayed on the display unit 430.

The state of the foods determined by the control unit 420 may be displayed on the display unit 430 provided at the refrigerator 400. For example, when the target food is kimchi, the control unit 420 can determine the state of the kimchi as one of raw kimchi, medium, well-done, and acidified according to the output signal of the optical sensor 410, and the determination result can be displayed on the display unit 430 such that the user can check the current state of the kimchi.

Alternatively, when the target food is meat, the control unit 420 can determine the state of the meat as one of a mature operation and a decay operation according to the output signal of the optical sensor 410, or further can determine when the meat is most delicious, and the result can be displayed on the display unit 430.

As described above, because the gas sensor 200 can have reversibility, the gas sensor 200 can be continuously used during the lifetime of the refrigerator 400.

Meanwhile, the refrigerator 400 may be provided to control the temperature of a storage chamber 403 configured to store foods in a main body 407 and actively manage the state of the foods, without being limited to display of the state of the target food.

Figure 18:
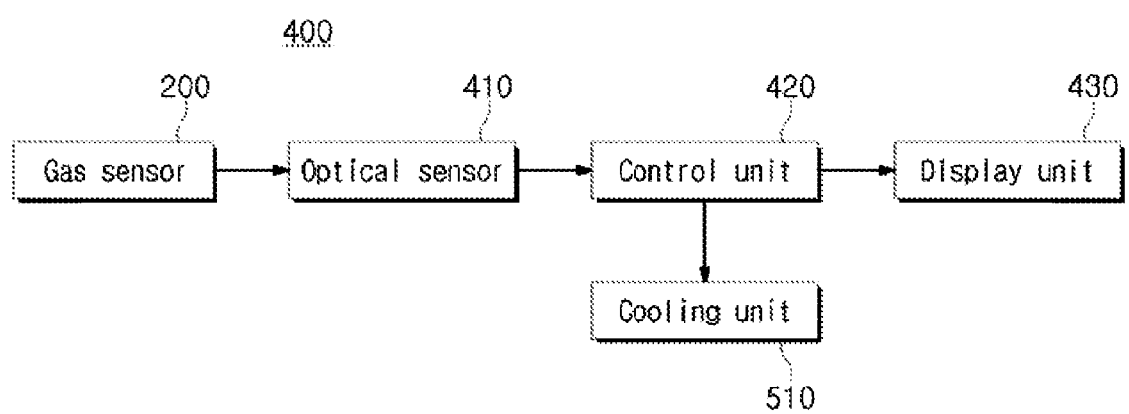
FIG. 18 is a control block diagram of a refrigerator according to an embodiment configured to control a temperature thereof.

FIG. 18 is a control block diagram of a refrigerator 400 according to an embodiment provided to control a temperature thereof. FIG. 18 also describes an example of the case in which the gas sensor 200 including the porous membrane M is applied to the refrigerator 400.

Referring to FIG. 18, the refrigerator 400 according to an embodiment may include a cooling unit 510 configured to supply a cold air into the storage chamber, in addition to the gas sensor 200, the optical sensor 410, the control unit 420, and the display unit 430, which are components of FIG. 15. In the gas sensor 200, the optical sensor 410, and the display unit 430, the configuration thereof is substantially the same as that of FIG. 15, and overlapping description thereof will be omitted. In addition, overlapping description of the control unit 420 related to FIG. 15 will also be omitted.

The control unit 420 can determine the state of the foods based on the output signal of the optical sensor 410, and can control the temperature of the storage chamber according to the determination result. In order to control the temperature of the storage chamber, the control unit 420 transmits a control signal to the cooling unit 510.

The control unit 420 can autonomously determine an appropriate temperature of the storage chamber corresponding to the current state of the foods according to the previously stored database. For example, when the target food is meat, the control unit 420 can recognize the temperature of the storage chamber at which the temperature arrives at an optimally matured state or the state can be maintained when the meat is in the mature operation other than the decay operation, and can transmit the control signal corresponding thereto to the cooling unit 510.

The control unit 420 can receive an order about the state of the foods from a user through the input unit, and can control the temperature of the storage chamber. For example, when the target food is kimchi and an order of maintaining the kimchi in the well-done state is input by the user, the control unit 420 can determine the temperature of the storage chamber at which the kimchi can be maintained in the well-done state, and can transmit the control signal corresponding thereto to the cooling unit 510.

Next, a method of controlling an electronic product according to an embodiment will be described.

Figure 19:
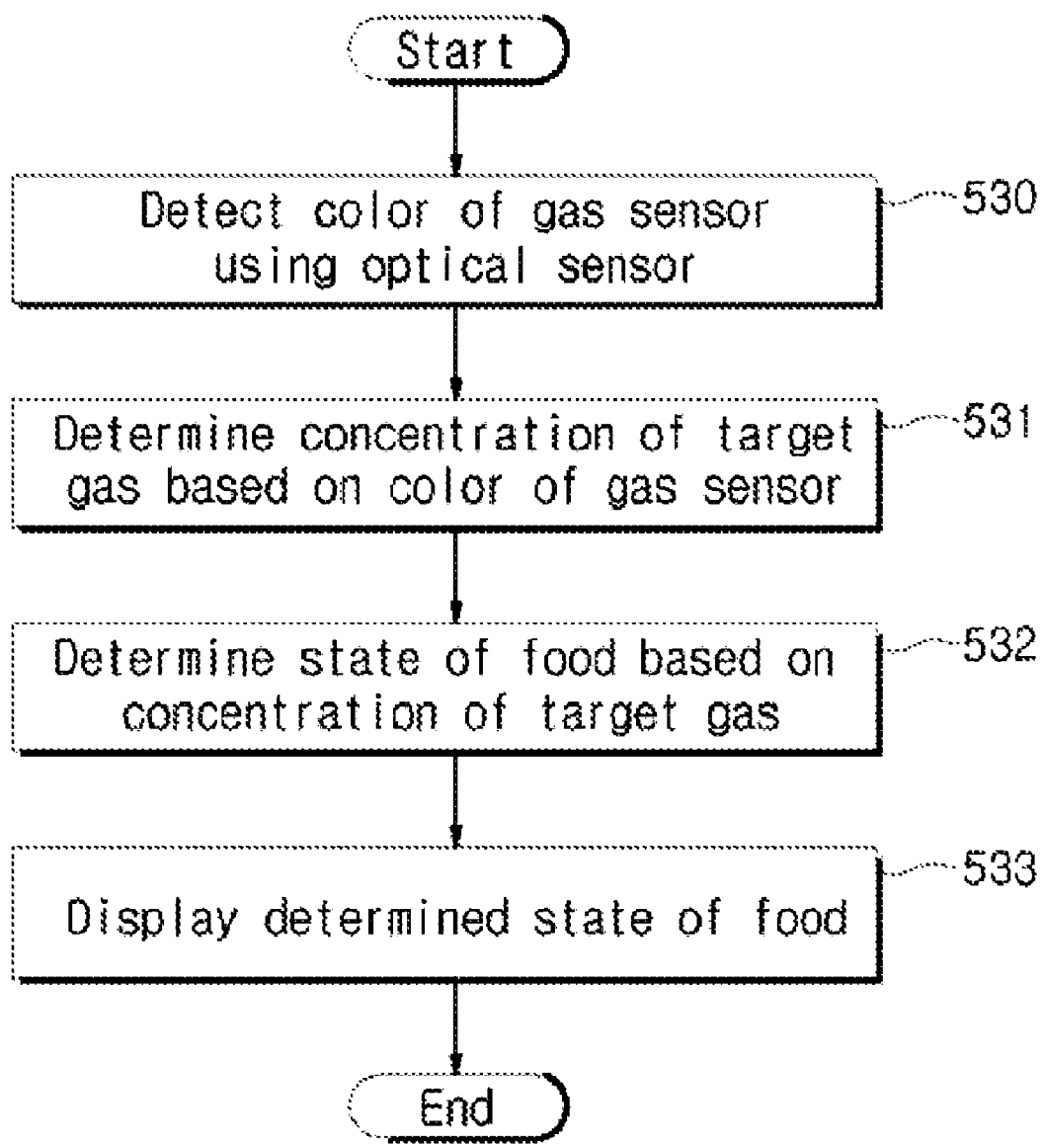
FIG. 19 is a flowchart showing a method of controlling an electronic product according to an embodiment.

FIG. 19 is a flowchart for describing a method of controlling the electronic product according to the embodiment. In the control method according to the embodiment, the electronic product according to the embodiment of FIGS. 15 to 17 may be applied, and hereinafter, the electronic product is the refrigerator 400.

Referring to FIG. 19, colors of the gas sensors 100 and 200 are detected using the optical sensor 410 (operation 530). A pH change of the hydrogel distribution liquid according to the concentration of the target gas is represented as a color change of the dye C. The colors of the gas sensors 100 and 200 can be detected using the optical sensor 410 mounted at a position corresponding to the gas sensors 100 and 200.

The concentration of the target gas is determined based on the colors of the gas sensors 100 and 200 (operation 531). Because the gas sensors 100 and 200 are attached to the inside of the storage container 405 having a transparent material, the color change of the dye C is seen from the outside. Because the color change of the dye C is in proportion to the concentration of the target gas, the concentration of the target gas can be determined through the color change of the dye C.

The state of the foods is determined based on the concentration of the target gas (operation 532), and the determined state of the foods is displayed (operation 533). Because the description is the same as above, overlapping description thereof will be described.

Figure 20:
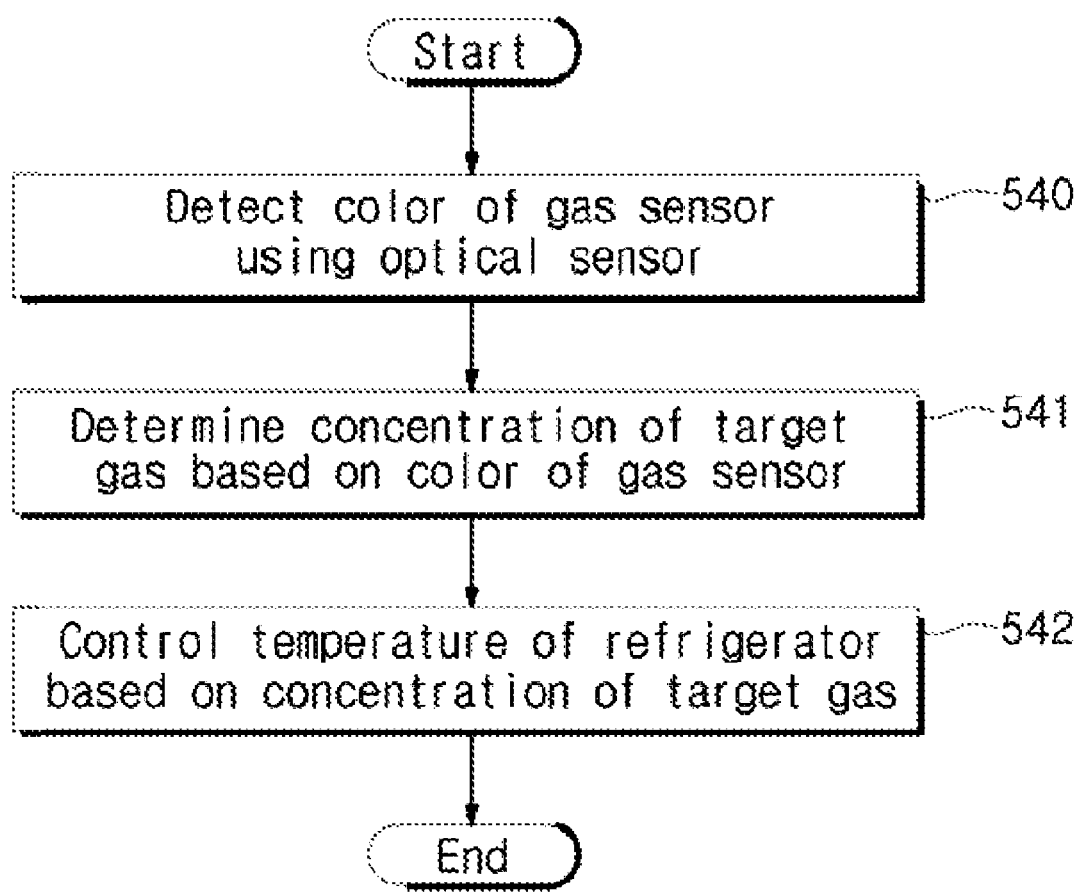
FIG. 20 is a flowchart showing a method of controlling an electronic product according to an embodiment, specifically, a temperature of a refrigerator.

FIG. 20 is a flowchart for describing a method of controlling a temperature of the refrigerator 400 according to an embodiment.

Referring to FIG. 20, the colors of the gas sensors 100 and 200 are detected using the optical sensor 410 (operation 540), and the concentration of the target gas is determined based on the colors of the gas sensors 100 and 200 (operation 541).

In addition, a temperature of the refrigerator 500 is controlled based on the concentration of the target gas (operation 542). The control unit can autonomously determine an appropriate temperature corresponding to the current state of the foods according to the previously stored database, or can receive an order about the state of the foods from a user and determine a temperature to arrive at the input state of the foods or to maintain the state.

According to the gas sensors 100 and 200, the electronic product including the gas sensor, and the method of controlling the electronic product, the target gas can be detected with good selectivity and resolution by dissolving the hydrogel in the dispersion medium and measuring the pH change of the dispersion medium.

According to the gas sensor having the above-mentioned configuration, the following effects can be expected.

First, because the gas sensor can be provided through only curing of the hydrogel without a separate sensor manufacturing process, a sensor manufacturing process can be minimized.

In addition, because various shapes of the gas sensor can be implemented according to the method of solidifying the hydrogel, restrictions in the manufacturing process can also be minimized.

In addition, as a natural material is used, biocompatibility can be maximized.

In addition, because the hydrogel has a moisture-containing property in itself, a separate structure for removing humidity upon manufacture of the sensor can be omitted.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A refrigerator comprising:
    a storage chamber;
    a cooling unit configured to supply cold air into the storage chamber;
    a gas sensor configured to determine a state of a food in the storage chamber, the gas sensor comprising:
        a hydrogel support including a dye configured to change color based on a pH change due to a reaction with a target gas;
        an optical sensor configured to detect the color of the dye; and
        a control unit configured to determine a state of a target food based on the color detected by the optical sensor and to control a temperature of the refrigerator by providing a control signal to the cooling unit according to the determined state of the target food,
    wherein the hydrogel support includes a hydrogel including at least one of agar, agarose, sodium alginate, potassium alginate, rubidium alginate, calcium alginate, barium alginate, and propylene glycol alginate.

2. The refrigerator according to claim 1, wherein the dye of the gas sensor comprises at least one of a natural dye and a synthetic dye.

3. The refrigerator according to claim 2, wherein the natural dye comprises an anthocyanin-based dye.

4. The refrigerator according to claim 2, wherein the natural dye comprises a dye extracted from at least one of red cabbage, blueberry, apple, pear, peach, asparagus, strawberry, pomegranate, and grape.

5. The refrigerator according to claim 2, wherein the synthetic dye comprises at least one of chlorophenol red, methyl red, bromothymol blue, bromocresol green, nitrophenol, bromocresol purple, and alizarin.

6. The refrigerator according to claim 1, wherein the target gas of the gas sensor comprises at least one of a volatile organic acid and a base.

7. The refrigerator according to claim 6, wherein the volatile organic acid comprises at least one of carbon dioxide and acetic acid, and
    the base comprises ammonia.

8. The refrigerator according to claim 1, wherein the hydrogel support of the gas sensor is provided to solidify a hydrogel.

9. The refrigerator according to claim 1, wherein the hydrogel support of the gas sensor has a cross-linked structure formed by a cross linking agent comprising a divalent cation.

10. The refrigerator according to claim 9, wherein the divalent cation comprises calcium ion, and
    the cross linking agent comprises calcium chloride.

11. The refrigerator according to claim 1, wherein the hydrogel of the hydrogel support of the gas sensor comprises natural hydrogel.

12. The refrigerator according to claim 1, wherein the hydrogel support of the gas sensor comprises at least one of glycerin, glycerol, propylene glycol, sorbitol, maltitol, polydextrose, triacetylglycerol, potassium lactate, isomalt, xylitol, sodium lactate, urea, glycosaminoglycan, poly vinyl alcohol, calcium chloride, and sodium chloride.

13. The refrigerator according to claim 1, wherein the gas sensor is manufactured in a sheet.

14. The refrigerator according to claim 13, further comprising a membrane coupled to one surface of the hydrogel support provided to contact the target gas.

15. The refrigerator according to claim 1, wherein the gas sensor is used to measure at least one of a freshness, a degree of maturity, and a degree of fermentation of foods.

16. The refrigerator according to claim 1, further comprising:
    a storage container comprising a transparent section,
    wherein the gas sensor is disposed inside the transparent section of the storage container.

17. The refrigerator according to claim 1, further comprising:
    a display unit configured to display the determined state of the food.

18. The refrigerator according to claim 1, wherein the control unit stores information about a relation between a signal output from the optical sensor and the state of the food, and determines the state of the food according to the stored information.

* * * * *